(12) United States Patent
Bara

(10) Patent No.: US 6,497,891 B2
(45) Date of Patent: Dec. 24, 2002

(54) MAKE-UP COMPOSITIONS

(75) Inventor: Isabelle Bara, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/971,590

(22) Filed: Oct. 9, 2001

(65) Prior Publication Data

US 2002/0061321 A1 May 23, 2002

(30) Foreign Application Priority Data

Oct. 9, 2000 (FR) .............................................. 00 12882

(51) Int. Cl.$^7$ .......................... A61K 9/18; A61K 7/021; A61K 47/30; A61L 15/22; A61L 15/60
(52) U.S. Cl. ...................... 424/401; 424/443; 424/484; 424/488; 424/499; 424/500; 424/70.14; 424/70.16; 424/70.11; 424/70.12; 424/63; 424/61; 424/64
(58) Field of Search ........................... 514/844; 424/61, 424/63, 69, 443, 401, 484, 488, 499, 500, 70.14, 70.16, 70.11, 70.12, 64

(56) References Cited

U.S. PATENT DOCUMENTS

| | | | |
|---|---|---|---|
| 3,639,572 A | 2/1972 | Heinrich et al. | 424/63 |
| 4,158,053 A | 6/1979 | Greene et al. | 424/61 |
| 5,306,487 A | 4/1994 | Karapasha et al. | 424/76.6 |
| 5,650,159 A * | 7/1997 | Lion et al. | 424/401 |

FOREIGN PATENT DOCUMENTS

JP 2000-143480 A * 11/1998

OTHER PUBLICATIONS

Database Chemical Abstracts, Access No. 132: 339 081, XP002170501, JP 2000 143480, May 23, 2000.

* cited by examiner

Primary Examiner—Edward J. Webman
Assistant Examiner—Helen Nguyen
(74) Attorney, Agent, or Firm—Finnegan, Henderson, Farabow, Garrett & Dunner, L.L.P.

(57) ABSTRACT

Cosmetic compositions comprising, in a cosmetically acceptable medium, at least one film-forming polymer and at least one water-superabsorbent polymer in the form of water-swelled particles, the mean size of which is at least about 0.5 mm. Procedures for making-up a keratinous material comprising applying the composition onto the keratinous material.

24 Claims, No Drawings

MAKE-UP COMPOSITIONS

The present invention is generally directed to cosmetic compositions comprising at least one film-forming polymer and particles of at least one water-superabsorbent polymer. The present invention is also directed to procedures for making-up a keratinous material. The present compositions and making-up procedures may be used for making-up a keratinous material such as skin, including the lips and scalp, and integuments such as the nails, hair, eyelashes and eyebrows of human beings. The present compositions may take the form of make-up for the body, facial skin, ears, including the lobe, as well as the lips, eyelashes, nails, and hair.

Make-up products are generally used to impart color, to highlight certain parts of the skin or integuments, or to obtain a glossy, matte, or satin appearance on the skin or integuments. Such products are usually applied in the form of a thin, uniform layer.

The use of aqueous dispersions of film-forming polymers to impart to the make-up product good durability on the skin or integuments is known. For example, U.S. Pat. No. 3,639,572 describes a make-up composition comprising an aqueous dispersion of polymer such as polyacrylate esters. After drying, this composition is said to leave a film of good durability on the skin. As another example, U.S. Pat. No. 4,158,053 describes nail varnishes comprising an aqueous dispersion of acrylic polymer for forming a film to adhere to the nails.

With the progress of fashion, consumers have become more demanding, and today desire new make-up products to produce original or special results, such as visible transformations of the made-up face or body. However, the make-up compositions currently available on the market generally produce a uniform and smooth film, but not make-up in relief, or in three-dimensional form. A need therefore exists for a make-up product that on application to the skin or integuments results in a make-up effect different from the uniform and smooth films currently obtained with the products available on the market.

The present invention is directed to make-up compositions that can produce a three-dimensional, or relief, make-up on the skin and on the integuments. The inventors have surprisingly found that a new type of make-up for a keratinous material can be obtained by producing a composition comprising at least one film-forming polymer and particles of at least one water-superabsorbent polymer. The compositions according to the invention thus lead to the formation of a three-dimensional deposit on the keratinous materials. The three-dimensional deposit is obtained on application of the present compositions onto keratinous materials. This deposit contains individual particles of the at least one water-superabsorbent polymer, which can resemble crystals, and which can give the appearance of jewels. In this way, it is possible to create the appearance of jewels on the skin and the integuments without using expensive precious stones. And, the compositions of the present invention have the added benefit of thickening eyelashes upon application.

The present invention is directed to a cosmetic composition comprising, in a cosmetically acceptable medium, at least one film-forming polymer, in combination with at least one water-superabsorbent polymer in the form of water-swelled particles having a mean size of at least about 0.5 mm. The present invention is also directed to a cosmetic procedure for making-up a keratinous material comprising application of a composition, such as those described herein, onto the keratinous material. An embodiment of the present invention is further directed to the use of a composition, such as those described herein, to obtain a make-up for a keratinous material, which creates the appearance of crystals and/or jewels.

An embodiment of the present invention is also directed to the use, in a cosmetic composition, of at least one film-forming polymer and of particles of at least one water-superabsorbent polymer in the form of water-swelled particles having a mean size of at least about 0.5 mm, to obtain a make-up for keratinous materials that presents the appearance of crystals and/or jewels. Another embodiment of the present invention is directed to the use of compositions, such as defined herein, to thicken the eyelashes. The present invention is further directed to the use, in a cosmetic composition, of at least one film-forming polymer and of particles of at least one water-superabsorbent polymer in the form of water-swelled particles having a mean size of at least about 0.5 mm, to thicken the eyelashes.

As used herein, "water-superabsorbent polymer" defines a polymer capable in its dry state of absorbing and retaining at least 20 times its weight in distilled water, and generally, in aqueous fluids. These polymers have a large capacity for absorption and retention of water, and of aqueous fluids generally. After absorption of the aqueous fluid, the particles of the polymer thus impregnated with aqueous fluid remain insoluble in the aqueous fluid and thus retain their individual particulate state. Water-superabsorbent polymers are generally described, for example, in *Absorbent Polymer technology, Studies in polymer science* 8 (L. Brannon-Pappas and R. Harland, eds., Elsevier, 1990).

As used herein, spontaneous absorption is intended to mean an absorption time of up to about 30 minutes. The water-superabsorbent polymer may have a water-absorbing capacity of from 20 times to about 2000 times its own weight (i.e., 20 g to about 2000 g of water absorbed per gram of absorbent polymer). In certain embodiments, the water-absorbing capacity of the polymer may range from about 30 to about 1500 times its own weight, or from about 50 to about 1000 times its own weight. These water-absorbing properties are defined under normal conditions of temperature (25° C.) and pressure (760 mm Hg, i.e., 100,000 Pa) and for distilled water.

The size of the water-superabsorbent polymer particles mentioned is the size of these particles after swelling of the polymer in water. The water-superabsorbent polymer particles, swelled with water, have a mean size greater than about 0.5 mm, and their size generally ranges from about 0.5 mm to about 20 mm. In certain embodiments, the size may also range from about 1 mm to about 15 mm or from about 3 mm to about 10 mm.

Examples of water-superabsorbent polymers include, but are not limited to:

polymers resulting from polymerization with partial crosslinking of water-soluble ethylenically unsaturated monomers, such as acrylic or vinylic polymers, and such polymers would include crosslinked and neutralized polyacrylates;

starch-grafted polyacrylates;

acrylamide/acrylic acid copolymers, including sodium salts of such polymers;

starch-grafted acrylamide/acrylic acid, including sodium and potassium salts of such polymers;

isobutylene/maleic anhydride copolymers;

sodium and potassium salts of carboxymethylcellulose;

crosslinked salts of polyaspartic acid; and chitosan/polyvinylpyrrolidone and chitosan/polyethyleneimine combinations.

Commercially available water-superabsorbent polymers include, but are not limited to:

crosslinked sodium or potassium polyacrylates, sold under the names SALSORB CL10, SALSORB CL20, "FSA type 101," and "FSA type 102," by the company Allied Colloids, ARASORB S-310, from Arakawa Chemical, "ASAP 2000" and ARIDALL 1460, from Chemdal, "KI-gel 201K," from Siber Hegner, AQUALIC CA W3, AQUALIC CA W7, and AQUALIC CA W10, from Nippon Shokubai, AQUA KEEP D 50, AQUA KEEP D 60, AQUA KEEP D 65, AQUA KEEP S 30, AQUA KEEP S 35, AQUA KEEP S 45, AQUA KEEP A1 M1, and AQUA KEEP A1 M3, from Atochem, and SANWET IM-5000D, from Hoechst Celanese;

starch-grafted polyacrylates, sold under the names SAN-WET IM-100, SANWET IM-3900, and SANWET IM-5000S, from Hoechst;

starch-grafted acrylamide/acrylic acid copolymers, in the form of the sodium or potassium salt, sold under the names WATERLOCK A-100, WATERLOCK A-200, WATERLOCK D-200, and WATERLOCK B-204, from Grain Processing Corporation;

acrylamide/acrylic acid copolymers, in the form of the sodium salt, sold under the name WATERLOCK G-400, from Grain Processing Corporation;

isobutylene/maleic anhydride copolymer, sold under the name "KI Gel-201 K";

carboxymethylcellulose, sold under the name AQUA-SORB A250, from Aqualon; and chitosan/polyvinylpyrrolidone combinations, sold under the name "Hydrogel AQUATRIX 2," and chitosan/polyethyleneimine combinations, sold under the name "Hydrogel AQUATRIX 3," from Hydromer.

The water-superabsorbent polymer may be present in the inventive compositions in an amount ranging from about 0.1 to about 50% by weight, relative to the total weight of the composition, or from about 0.5 to about 40% by weight, or from about 1 to about 30% by weight.

The compositions according to the invention contain at least one film-forming polymer to provide for cohesion and holding of the water-superabsorbent polymer particles on the keratinous materials. Owing to the film-forming property of the polymer, this polymer is different from the water-superabsorbent polymer, which is not film-forming.

As used herein, "film-forming polymer" is intended to mean a polymer capable of forming by itself, or in the presence of an auxiliary film-forming agent, a film, which may be continuous, adhering to a support, such as to a keratinous material. A film-forming polymer in the form of particles in aqueous dispersion, generally known under the name of latex or pseudolatex, may be used. Film-forming polymers that may be used in the compositions of the present invention include, but are not limited to, synthetic polymers of the radical type or polycondensate type, polymers of natural origin, and mixtures thereof. A "radical" film-forming polymer is intended to mean a polymer that may be obtained from ethylenically unsaturated monomers, each monomer being capable of homopolymerizing (i.e., this is in contradistinction to polycondensates).

Film-forming polymers of the radical type may be vinylic polymers or copolymers, and may be acrylic polymers. A vinylic film-forming polymer may be produced by the polymerization of ethylenically unsaturated monomers having at least one acid group and/or of esters of these acidic monomers and/or of amides of these acid monomers. As monomers bearing an acid group, α,β-ethylenically unsaturated carboxylic acids including, but not limited to, acrylic acid, methacrylic acid, crotonic acid, maleic acid and itaconic acid, may be used. (Meth)acrylic acid and crotonic acid, or more simply (meth)acrylic acid, may be used in certain embodiments.

The esters of acidic monomers may be selected, for example, from esters of (meth)acrylic acid (also called (meth)acrylates). This group includes, but is not limited to, alkyl, such as $C_1$–$C_{20}$ or $C_1$–$C_8$ alkyl (meth)acrylates, aryl, such as $C_6$–$C_{10}$ aryl (meth)acrylates, and hydroxyalkyl, such as $C_2$–$C_6$ hydroxyalkyl (meth)acrylates. Among the alkyl (meth)acrylates, methyl methacrylate, ethyl methacrylate, butyl methacrylate, isobutyl methacrylate, 2-ethylhexyl methacrylate, and lauryl methacrylate are provided as nonlimiting examples. Among the hydroxyalkyl (meth) acrylates, hydroxyethyl acrylate, 2-hydroxypropyl acrylate, hydroxyethyl methacrylate, and 2-hydroxypropyl methacrylate are provided as nonlimiting examples. And among the aryl (meth)acrylates, benzyl acrylate and phenyl acrylate are provided as nonlimiting examples. In certain embodiments, alkyl (meth)acrylates are the esters of (meth)acrylic acid that are used.

According to the present invention, the alkyl group of the esters may be fluorinated, and for example, may be perfluorinated. That is, fluorine atoms may replace some or all of the hydrogen atoms of the alkyl groups.

As nonlimiting examples of amides of acidic monomers, (meth)acrylamides, including N-alkyl, such as $C_2$–$C_{12}$ alkyl (meth)acrylamides, are provided. Among the N-alkyl (meth) acrylamides, N-ethylacrylamide, N-t-butylacrylamide and N-t-octylacrylamide are provided as nonlimiting examples.

Vinylic film-forming polymers may also result from the homopolymerization or copolymerization of monomers such as vinyl esters and/or styrenic monomers. These monomers may be polymerized with acidic monomers and/or esters thereof and/or amides thereof, and those mentioned above are provided as nonlimiting examples. Vinyl esters include, but are not limited to, vinyl acetate, vinyl neodecanoate, vinyl pivalate, vinyl benzoate, and vinyl t-butylbenzoate. Styrenic monomers include, but are not limited to, styrene and alpha-methylstyrene.

The list of monomers provided herein is not limiting and it is, of course, possible to use any monomer that comes within the categories of acrylic and/or vinylic monomers, including monomers modified with a silicone chain.

Commercially available acrylic film-forming polymers usable according to the invention include, but are not limited to, NEOCRYL XK-90®, NEOCRYL A-1070®, NEOCRYL A-1090®, NEOCRYL BT-62®, NEOCRYL A-1079®, and NEOCRYL A-523®, from Avecia-Neoresins, and Dow Latex 432®, from Dow Chemical.

Polycondensates usable as film-forming polymers include, but are not limited to, anionic, cationic, non-ionic and amphoteric polyurethanes, polyurethane-acrylics, polyurethane-polyvinylpyrrolidones, polyester-polyurethanes, polyether-polyurethanes, polyureas, polyurea/polyurethanes, and mixtures thereof can also be used.

As nonlimiting examples, the at least one film-forming polymer may be chosen from aliphatic, cycloaliphatic and aromatic polyurethanes, polyurea/urethanes, and polyurea copolymers. These polymers may include sequences derived from aliphatic monomers, cycloaliphatic monomers, and aromatic polyester monomers, branched and unbranched silicone sequences, such as polydimethyl-siloxane and polymethylphenylsiloxane, and sequences having fluorinated groups.

The film-forming polyurethanes such as defined in the invention can also be obtained from monomers chosen from branched and unbranched polyesters and from alkyds having mobile hydrogens that are modified by reaction with a diisocyanate and a bifunctional organic compound, such as, for example, dihydroxy, diamino, or hydroxyamino. The polyesters and alkyds may have, in addition, at least one of a carboxylic acid, a carboxylate group, a sulphonic acid, a sulphonate group, a neutralizable tertiary amine group, and a quaternary ammonium group.

Commercially available film-forming polyurethanes usable according to the invention include, but are not limited to, NEOREZ R-981® and NEOREZ R-974® by the company Avecia-Neoresins, and AVALURE UR-405®, AVALURE UR-410®, SANCURE 875®, SANCURE 2060®, AVALURE UR425®, AVALURE UR-430®, SANCURE 861®, SANCURE 878® and AVALURE UR-450® by the company Goodrich.

Examples of film-forming polycondensates usable in the present invention include, but are not limited to, polyesters, polyester amides, fatty-chain polyesters, polyamides, and epoxy ester resins. The polyesters can be obtained, by using known procedures, by polycondensation of dicarboxylic acids with polyols, including diols.

The dicarboxylic acids may be chosen, for example, from aliphatic, alicyclic, and aromatic dicarboxylic acids. As nonlimiting examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornane dicarboxylic acid, diglycolic acid, thiodipropionic acid, 2,5-naphthalenedicarboxylic acid, and 2,6-naphthalenedicarboxylic acid, are provided. These dicarboxylic acid monomers may be used alone or in combinations of at least two dicarboxylic acid monomers. Among these monomers, phthalic acid, isophthalic acid, and terephthalic acid may be used in certain embodiments.

Diols may be chosen from among the aliphatic, alicyclic and aromatic diols, for example. Specific examples include ethylene glycol, diethylene glycol, triethylene glycol, 1,3-propanediol, cyclohexanedimethanol, and 4-butanediol. Nonlimiting examples of other polyols include glycerol, pentaerythritol, sorbitol, and trimethylolpropane.

Polyester amides may be obtained in an analogous manner to the polyesters, by polycondensation of diacids with compounds chosen from diamines and amino alcohols. Nonlimiting examples of diamines include ethylenediamine, hexamethylenediamine, and meta- and para-phenylenediamine. As a nonlimiting example of an amino alcohol, monoethanolamine is provided.

The polyester may, in addition, contain at least one monomer bearing at least one —$SO_3M$ group, wherein M is chosen from hydrogen, an ammonium ion, $NH_4^+$, and metal ions, such as, for example, $Na^+$, $Li^+$, $K^+$, $Mg^{2+}$, $Ca^{2+}$, $Cu^{2+}$, $Fe^{2+}$ and $Fe^{3+}$.

In addition, a bifunctional aromatic monomer having such an —$SO_3M$ group may be used. The aromatic nucleus of the bifunctional aromatic monomer additionally bearing an —$SO_3M$ group may, for example, be chosen from benzene, naphthalene, anthracene, diphenyl, oxydiphenyl, sulphonyidiphenyl, and methylenediphenyl groups, but it is not limited to these moieties. Examples of bifunctional aromatic monomers additionally bearing an —$SO_3M$ group include, but are not limited to, sulphoisophthalic acid, sulphoterephthalic acid, sulphophthalic acid, and 4-sulphonaphthalene-2,7-dicarboxylic acid.

In the compositions of the present invention, copolymers based on isophthalate/sulphoisophthalate, and copolymers obtained by condensation of diethylene glycol, cyclohexanedimethanol, isophthalic acid, and/or sulphoisophthalic acid may be used. A commercially available example of such polymers includes, but is not limited to, EASTMAN AQ, by the company Eastman Chemical Products.

The polymers of natural origin, which may be modified, may be selected from among shellac resin, sandarac gum, dammar gums, elemi gums, copal resins, water-insoluble cellulosic polymers, and mixtures thereof, for example.

Polymers resulting from radical polymerization of one or several radical monomers in the interior and/or partially on the surface of pre-existing particles of at least one polymer selected from polyurethanes, polyureas, polyesters, polyester amides and/or alkyds may also be cited. These polymers are generally called hybrid polymers.

The skilled person, on the basis of his or her general knowledge, can prepare the dispersion containing at least one, i.e., one or more, film-forming polymers.

The size of the particles of the film-forming polymer in aqueous dispersion may range from about 10 to about 500 nm, or from about 20 to about 300 nm. The film-forming polymer may be present in the inventive compositions in an amount ranging from about 1% to about 50% by weight, or from about 5% to about 40% by weight, of the dry matter of film-forming polymers relative to the total weight of the composition. In some embodiments, the at least one film-forming polymer and the at least one water-superabsorbent polymer are present in the inventive compositions in a polymer/polymer weight ratio of from about 5:1 to about 15:1.

The compositions of the present invention may also contain an auxiliary film-forming agent, furthering the formation of a film with the particles of the film-forming polymer. Such a film-forming agent may be selected from any of the compounds known by the skilled person to be capable of fulfilling the desired function, including plasticizers and coalescing agents.

The medium of the compositions of the invention may be an aqueous medium containing water. The water content in the compositions may range from about 3% to about 98.9% by weight, relative to the total weight of the composition, or from about 10% to about 90% by weight.

The present compositions may also contain a thickener. Examples of thickeners usable according to the invention include, but are not limited to:

water-soluble cellulosic thickeners such as hydroxyethylcellulose, methylcellulose, and hydroxypropylcellulose. A commercially available example includes, but is not limited to, CELLOSIZE QP 44001H, from Amercol;

guar gum, such as those sold under the name VIDOGUM GH 175, from Unipectine, and JAGUAR C, from Meyhall;

quaternized guar gum, such as JAGUAR C-13-S, from Meyhall;

non-ionic guar gums containing $C_1$–$C_6$ hydroxyalkyl groups. Examples include, but are not limited to, hydroxymethyl, hydroxyethyl, hydroxypropyl and hydroxybutyl. Commercially available examples include, but are not limited to, JAGUAR HP8, JAGUAR HP60 and JAGUAR HP120, JAGUAR DC 293, and JAGUAR HP 105, from Meyhall, and GALACTASOL 4H4FD2, from Aqualon.

xanthan, carob, scleroglucan, gellan, rhamsan, and karaya gums;

alginates, maltodextrin, starch and derivatives thereof, hyaluronic acid and salts thereof;

clays, such as montmorillonites, hectorites and laponites;

crosslinked polyacrylic acids such as CARBOPOL, from Goodrich;

glyceryl poly(meth)acrylate polymers, such as those sold under the names HISPAGEL or LUBRAGEL by the companies Hispano Quimica or Guardian;

polyvinylpyrrolidone;

polyvinyl alcohol;

crosslinked polymers and copolymers of acrylamide, such as those sold under the names "PAS 5161" or BOZEPOL C, from Hoechst, and SEPIGEL 305, from Seppic;

crosslinked methacryloyloxyethyltrimethylammonium chloride homopolymers, such as those sold under the name SALCARE SC95, from Allied Colloid; and aggregating polymers, including aggregating polyurethanes.

In the compositions according to the invention, the thickener may be present in an amount ranging from about 0.1% to about 20% by weight, relative to the total weight of the composition, or from about 1% to about 10% by weight, relative to the total weight of the composition.

To further the rapid drying of the composition after its application onto the skin and/or the integuments, the inventive compositions may contain drying accelerators such as volatile solvents, including water-miscible volatile organic solvents, such as ethanol. The quantity of such organic solvents is generally selected such that the viscosity of the composition is maintained in the ranges described herein. These organic solvents may be present in the inventive compositions in an amount up to about 15% by weight, relative to the total weight of the composition, and may range from about 0.1% to about 15%, or the solvent may only be present at a content of up to about 10% by weight, or ranging from about 0.5% to about 10%. As used in this context, "volatile" is intended to mean a compound that is generally capable of evaporating upon contact with the skin, at ambient temperature.

The inventive compositions may also contain a water-soluble colorant. For example, a water-soluble colorant may be added to the water used to swell the water-superabsorbent polymer, which can result in colored crystals giving a beautiful jewel-like appearance. Examples of water-soluble colorants include, but are not limited to, 4-[(2,4-dimethylphenyl)azo]-3-hydroxy-2,7-naphthalene-disulfonic acid disodium salt, alizarin green disodium salt, brilliant blue disodium salt, quinoline yellow, amaranth trisodium salt, tartrazine disodium salt, rhodamine monosodium salt, fuchsine disodium salt, xanthophyll, and mixtures thereof can be cited.

The compositions of the present invention may, in addition, contain other ingredients normally used in cosmetics. For example, plasticizers, coalescing agents, fillers, coloring materials such as pigments and colorants, waxes, surfactants, preservatives, oils, hydrating agents, and perfumes, all of which are well-known in the state of the technology, may be included in the composition. Of course, the skilled person will take care to select any additive or additives and/or their quantity in such a way that at least one of the advantageous properties of three-dimensional deposition on the skin and/or the integuments is retained.

The present compositions may be applied to the skin by means of any applicator, including, but not limited to, fingers, brushes, foam-tipped applicators, flocked and felt pens, paintbrushes, and spatulas. The compositions of the invention may also be applied to the skin by means of a stencil: the composition thus deposited in the cut-out parts of the stencil retains its shape after the removal of the stencil, thus giving a very decorative make-up on the skin.

EXAMPLES

The invention is illustrated in more detail in the following example.

Example 1

A skin make-up composition comprising the following ingredients was prepared:

| | |
|---|---|
| water-superabsorbent polymer sold under the name SALSORB CL 10, from Allied Colloids | 2.5 g |
| aqueous polyurethane dispersion with 35% of polymer (AVALURE UR-405, from Goodrich) | 21 g (of active material) |
| brilliant blue disodium salt (blue colorant) | 0.001 g |
| preservative | qs |
| water | qsp 100 g |

The composition was prepared at ambient temperature by swelling the water-superabsorbent polymer in water with the colorant and preservative added, and then the polyurethane in aqueous dispersion was added to this mixture.

A make-up composition containing particles of water-superabsorbent polymer swelled with water displaying a particle size of from about 2 to about 5 mm was thereby obtained.

After application of the composition onto the skin, a make-up displaying the appearance of transparent bluish stones was obtained.

This composition applied to the eyelashes made it possible to thicken the latter.

What is claimed is:

1. A cosmetic composition comprising, in a cosmetically acceptable medium, at least one film-forming polymer and at least one water-superabsorbent polymer in the form of water-swelled particles having a mean size greater than 0.5 mm.

2. The composition according to claim 1, wherein the at least one water-superabsorbent polymer absorbs from 20 g to about 2000 g of water per gram of polymer on contact with water.

3. The composition according to claim 1, wherein the mean size of the water-swelled particles of the at least one water-superabsorbent polymer ranges from about 0.5 mm to about 20 mm.

4. The composition according to claim 3, wherein the mean size of the water-swelled particles of the water-superabsorbent polymer ranges from about 1 mm to about 15 mm.

5. The composition according to claim 4, wherein the mean size of the water-swelled particles of the water-superabsorbent polymer ranges from about 3 mm to about 10 mm.

6. The composition according to claim 1, wherein the at least one water-superabsorbent polymer comprises at least one component chosen from:

polymers resulting from polymerization of water-soluble ethylenically unsaturated monomers, with partial crosslinking;

starch-grafted polyacrylates;

acrylamide/acrylic acid copolymers;

starch-grafted acrylamide/acrylic acid;

isobutylene/maleic anhydride copolymers;

sodium and potassium salts of carboxymethylcellulose;

crosslinked salts of polyaspartic acid; and chitosan/polyvinylpyrrolidone and chitosan/polyethyleneimine combinations.

7. The composition according to claim 6, wherein the acrylamide/acrylic acid copolymers are chosen from sodium salts of acrylamide/acrylic acid copolymers.

8. The composition according to claim 6, wherein the starch-grafted acrylamide/acrylic acid is chosen from sodium and potassium salts of starch-grafted acrylamide/acrylic acid.

9. The composition according to claim 6, wherein the at least one water-superabsorbent polymer is chosen from crosslinked sodium polyacrylates.

10. The composition according to claim 1, wherein the at least one water-superabsorbent polymer is present in an amount ranging from about 0.1% to about 50% by weight, relative to the total weight of the composition.

11. The composition according to claim 10, wherein the at least one water-superabsorbent polymer is present in an amount ranging from about 0.5% to about 40% by weight, relative to the total weight of the composition.

12. The composition according to claim 1, wherein the at least one film-forming polymer is chosen from radical polymers, polycondensates, and polymers of natural origin.

13. The composition according to claim 1, wherein the at least one film-forming polymer is chosen from vinylic polymers resulting from polymerization of at least one monomer chosen from α,β-ethylenically unsaturated carboxylic acids, esters of α,β-ethylenically unsaturated carboxylic acids, amides of α,β-ethylenically unsaturated carboxylic acids, vinyl esters, and styrenic monomers.

14. The composition according to claim 1, wherein the at least one film-forming polymer is chosen from polyurethanes, polyesters, polyester amides, polyamides, and epoxy ester resins.

15. The composition according to claim 1, wherein the at least one film-forming polymer is chosen from shellac resin, sandarac gum, dammar gums, elemi gums, copal resins, and water-insoluble cellulosic polymers.

16. The composition according to claim 1, wherein the at least one film-forming polymer is in the form of an aqueous dispersion of particles.

17. The composition according to claim 1, wherein the at least one film-forming polymer is present in an amount ranging from about 1% to about 50% by weight, relative to the total weight of the composition.

18. The composition according to claim 1, further comprising a water-soluble colorant.

19. The composition according to claim 1, further comprising a thickener.

20. The composition according to claim 1, further comprising at least one additive chosen from plasticizers, coalescing agents, fillers, coloring materials, waxes, surfactants, preservatives, oils, hydrating agents, and perfumes.

21. A method for making-up a keratinous material comprising applying to the keratinous material a cosmetic composition comprising, in a cosmetically acceptable medium, at least one film-forming polymer and at least one water-superabsorbent polymer in the form of water-swelled particles having a mean size of greater than 0.5 mm.

22. A method of preparing a make-up composition, comprising:

swelling, in an aqueous fluid, at least one water-superabsorbent polymer to form water-swelled particles having a mean particle size of greater than 0.5 mm; and combining, in a cosmetically acceptable medium, at least one film-forming polymer and the water-swelled particles of the at least one water-superabsorbent polymer.

23. A method of thickening eyelashes, comprising:

applying a composition comprising, in a cosmetically acceptable medium, at least one film-forming polymer and at least one water-superabsorbent polymer in the form of water-swelled particles having a mean size of greater than 0.5 mm, to eyelashes.

24. An eyelash mascara composition comprising at least one film-forming polymer and at least one water-superabsorbent polymer in the form of water-swelled particles having a mean size of greater than 0.5 mm.

* * * * *